United States Patent [19]

Takada

[11] Patent Number: 4,561,427

[45] Date of Patent: Dec. 31, 1985

[54] ENDOSCOPE

[76] Inventor: Masazumi Takada, 403, Jinguumae 6-25-8, Shibuya-ku, Tokyo, Japan

[21] Appl. No.: 566,885

[22] Filed: Dec. 29, 1983

[30] Foreign Application Priority Data

Jan. 5, 1983 [JP] Japan ..................................... 58-673
Aug. 8, 1983 [JP] Japan ........................... 58-123349[U]

[51] Int. Cl.$^4$ ............................................. A61B 1/06
[52] U.S. Cl. ...................................................... 128/4
[58] Field of Search ...................................... 128/4–11

[56] References Cited

U.S. PATENT DOCUMENTS

| 2,067,031 | 1/1937 | Wappler | 128/5 |
| 3,190,286 | 6/1965 | Stokes | 128/6 |
| 3,557,780 | 1/1971 | Sato | 128/4 |
| 3,892,228 | 7/1975 | Mitsui | 128/4 |
| 3,948,251 | 4/1976 | Hosono | 128/6 X |

FOREIGN PATENT DOCUMENTS 2481915 11/1981 France .
2202483 9/1983 Japan .

Primary Examiner—William H. Grieb
Attorney, Agent, or Firm—Sandler & Greenblum

[57] ABSTRACT

This invention relates to an endoscope in which an endless belt is guided around via the interior and the exterior of an insertion tube of the endoscope and this endless belt is turned in contact with the body cavity wall surface, thereby enabling to insert the endoscope quickly.

The endless belt is guided around between a hole formed at the forward end portion of the insertion tube and a control portion at the proximal end of the insertion tube in a manner to be partially exposed to the outside of the insertion tube, while, a drive means for turning the endless belt is provided in the control portion.

12 Claims, 16 Drawing Figures

ENDOSCOPE

BACKGROUND OF THE INVENTION

1. Field of the Invention

This invention relates to an endoscope utilized for the diagnosis and inspection of a living body, and mainly, a body cavity and the interior of a hollow organ in a human body.

2. Description of the Prior Art

Heretofore, there have been widely utilized fiber scopes for diagnosis and inspection of a living body, and mainly, a body cavity and the interior of a hollow organ in a human body such for example as the interiors of an upper digestive tract from a gallet through a stomach to a duodenum, a small intestine and a large intestine, and as apparatuses for medical treatment.

However, since the fiber scope of the type described is to be directly inserted into a human body through a body cavity, various troubles may occur when the fiber scope is inserted into an organ disposed in a deep portion of the body. When a fiber scope for the small intestine is to be inserted into the small intestine through an oral cavity or an anus for example, if the fiber scope is pushed in, then the fiber scope does not advance in the small intestine, because the small intestine is afloat on a mesentery. Then, the small intestine advances together with the fiber scope, and, if the fiber scope is further forcedly pushed in, then there may be a danger of breaking the small intestine. On the other hand, when a fiber scope for the large intestine is inserted through the anus, if the fiber scope is forcedly pushed into the large intestine, then a sigmoid colon located upwardly of a rectum may be broken.

Therefore, except for the above-described method of forcedly inserting the fiber scope into the body, there have heretofore been practised methods of insertion including a sonde method of inserting the fiber scope through the utilization of peristaltic motion of the intestines, a rope-way method, in which a string having a diameter of about 2 mm is swallowed by a patient and a fiber scope is inserted by drawing the string discharged by the patient the next day, and the like. However, both the sonde method and the rope-way method are disadvantageous in that a long period of time is required for the insertion of the fiber scope and the insertion causes pains to the patient for that long period of time.

Now, in the specification of French Patent No. 2481915, there is disclosed an apparatus having a so-called self-running device, in which a pulley is provided on the outer surface portion of a head of fiber scope and a belt being in frictional contact with the body wall surface is guided around this pulley.

According to the French Patent, the insertion of the head can be made for a short period of time by the turning of the belt. However, since the pulley is considerably projected from the outer surface of the head, with the result that the head becomes large sized, so that the pains suffered by the patient should not necessarily be alleviated. Moreover, the apparatus according to the French Patent is disadvantageous in that, when the fiber scope is inserted into a portion to be inspected such as a sigmoid colon, a mucous coat of the intestine is liable to be hurt, thus resulting in unsatisfactory safelty.

In Japanese Patent Kokai (Laid-Open) No. 22024/83, there is disclosed a fiber scope, in which a pulley for supporting a belt being in frictional contact with the body wall surface is provided in a head and the belt is extended through a hole formed in this head portion.

In the fiber scope according to the Japanese Patent Kokai (Laid-Open) No. 22024/83, the provision of the pulley in the head makes it possible to lessen the value of the aforesaid projection. However, the provision of a drive means for turning the pulley in the head increases the head accordingly, whereby the pains suffered by the patient still cannot be removed.

SUMMARY OF THE INVENTION

The present invention has as its object the provision of an endoscope which can be readily inserted for a short period of time without giving great pains to a patient.

To achieve the above-described object, the present invention contemplates that at least one endless belt is guided around via the interior and the exterior of an insertion tube and a head in such a manner that the endless belt exposed from the outer surfaces of the insertion tube and the head is contacted with the outer surface of the insertion tube, and a drive means for turning this endless belt is provided at the proximal end of the insertion tube, to thereby lessen the diameters of the insertion tube and the head.

DETAILED DESCRIPTION OF THE PREFERRED EMBODIMENTS

Description will hereunder be given of the embodiments of the present invention with reference to the drawings.

Figure 1:
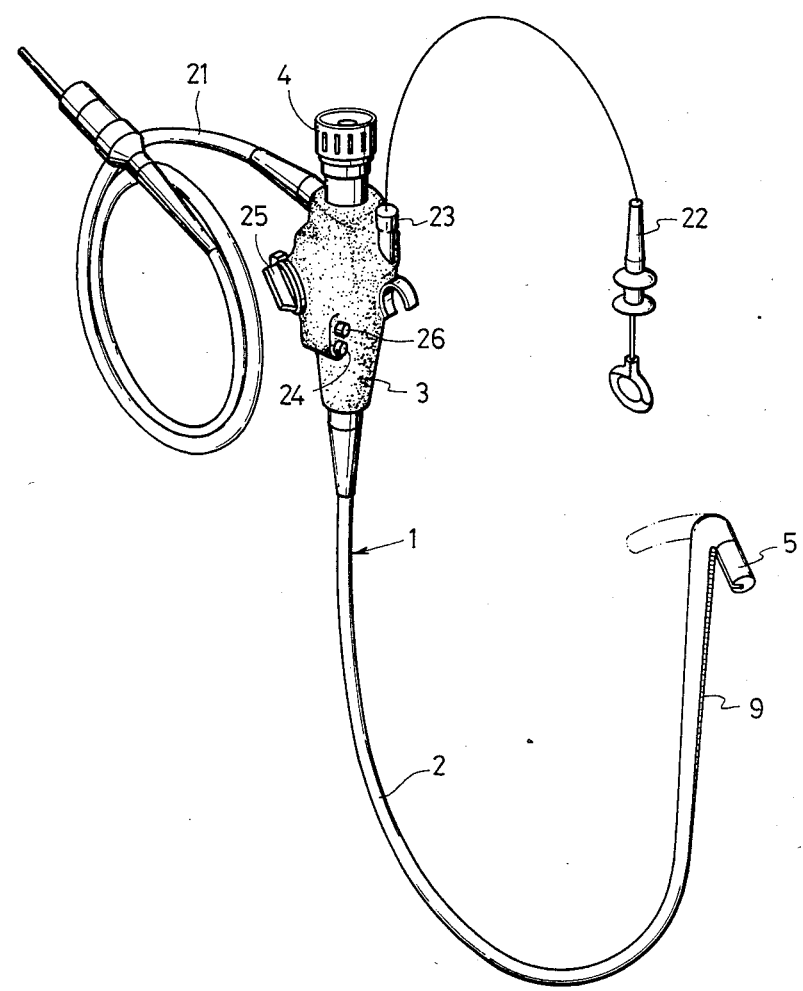
FIG. 1 a perspective view showing the general arrangement of a first embodiment of the endoscope according to the present invention.

FIG. 1 shows the general arrangement of the first embodiment of the endoscope according to the present invention.

In a fiber scope 1, an ocular poriton 4 is integrally formed on the proximal end portion of an insertion tube 2 formed into a small diameter tube made of a flexible material through a control portion 3.

Figure 2:
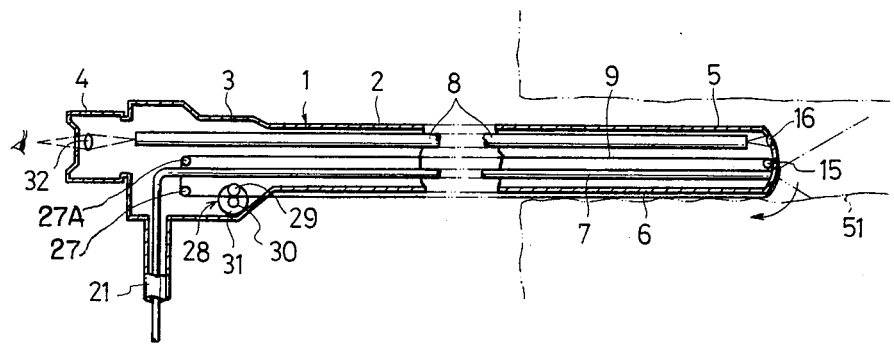
FIG. 2 is a sectional view thereof.
Figure 3:
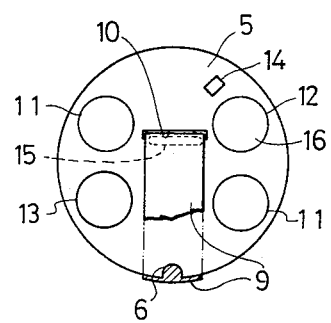
FIG. 3 is a front view showing the forward end face of head of the fiber scope in the first embodiment.

As shown in FIG. 2, the insertion tube 2 is formed at the forward end thereof with a head 5, provided on the outer surface, on one side and in the longitudinal direction thereof with a dovetail grooveshaped guide groove 6 (Refer to FIG. 3), and further, contains therein, in the longitudinal direction thereof, two light guides 7, in each of which a plurality of optical fibers are bundled, an image guide 8, in which a plurality of optical fibers are bundled, an endless belt 9 being partially turned along the guide groove 6 and made of a flexible material, a forceps guide tube, not shown, an air-water feed tube, and the like. As shown in FIG. 3, the head 5 is provided therein with a belt guide hole 10 for leading the endless belt 9 to outside. Around the belt guide hole 10, there are provided projector holes 11 at positions corresponding to the forward ends of the light guides 7, a picture hole 12 at a position corresponding to the forward end of the image guide 8, a forceps hole 13 at a position diagonal to this picture hole 12 and an air-water feed hole 14 at a position adjacent to the picture hole 12, respectively. Inside the belt guide hole 10, there is provided a guide roller 15 for guiding the endless belt 9 from the outer end face of the head 5 to the guide groove 6. Furthermore, the picture hole 12 is fitted therein with an objective lens 16 for focusing the rays from outside and causing the same to be incident on the image guide 8.

Outside the control portion 3, there are provided a flexible connection tube 21 for connecting the light guides 7 to a light source device, not shown, a forceps insertion hole 23 for projecting a forceps 22 (Refer to FIG. 1) from the forceps hole 13 through a forceps guide tube of the insertion tube 2, an air-water feed hole portion 24 and an water suction hole 26 for flowing air and washing water out of the air-water feed hole 14 through a water conveying tube of the insertion tube 2 and washing the objective lens 16, and a control knob 25 for flexing the forward end portion (head 5) of the insertion tube 2, respectively. Furthermore, inside the control portion 3, there are provided two guide rollers 27A, 27 for guiding the proximal end of the endless belt 9 and a drive means 28 for turning the endless belt 9, respectively. The drive means 28 comprises a pair of clamp rollers 29, 30 for clamping the opposite surfaces of the endless belt 9 and a motor 31 for driving one 30 of the clamp rollers.

Inside the ocular portion 4, there is provided an ocular lens 32 for focusing the rays emitted from the proximal end of the image guide 8, whereby an image made to focus at the forward end of the image guide 8 by the objective lens 16 is transmitted to the proximal end of the image guide 8 through the optical fibers of the image guide 8 and inspected through the ocular lens 32.

The method of use will now be described. To insert the fiber scope 1 through a body cavity, e.g., an anus, firstly one 30 of the clamp rollers is rotated by the driving of the motor 31 to thereby turn the endless belt 9 in a direction indicated by an arrow mark as shown in FIG. 2. When the forward end of the insertion tube 2 is inserted through an anus in this state, the endless belt 9 exposed from the forward end portion of the insertion tube 2 comes into contact with a part of a body cavity wall 51 as shown in FIG. 2, so that the insertion tube 2 can be inserted along the body cavity wall 51 due to the contact resistance. Thus, even if the portion of the body cavity is curved or is a comparatively weak mucosa layer such as an intestine, the forward end of the insertion tube 2 is guided along the body cavity wall, so that the insertion tube 2 can be inserted into a deep portion of the interior of the body with no body cavity wall being broken.

In consequence, according to this embodiment, the endless belt 9 partially exposed from the outer surface of the forward end portion to the proximal end portion of the fiber scope 1 is brought into contact with the fiber scope 1 in a manner to be slidable on the outer surface of the insertion tube 2 and the drive means 28 for turning the endless belt 9 is provided in the control portion 3, so that the outer diameter of the insertion tube 2, particularly, the outer diameter of the head 5 can be reduced. Moreover, when the forward end of the fiber scope 1 is inserted through a body cavity in the conditions where the endless belt 9 if turned by the drive means 28, the fiber scope 1 is inserted into the body, while being guided along the body cavity wall 51, due to the contact resistance caused between the endless belt 9 and the body cavity wall 51, so that the fiber scope 1 can be inserted quickly and with no considerable pains given to the patient. Further, according to this embodiment, the endless belt 9 is exposed over the total length of the outer surface of the insertion tube 2, whereby, the larger the length of insertion of the insertion tube 2 into the body becomes, the larger the contact surface between the body cavity wall and the endless belt 9 becomes, so that the fiber scope 1 can be readily inserted into the deep portion in the body with no excessively large contact resistance given to a part of the body cavity wall. Since the endless belt 9 is guided by the guide groove 6, the endless belt 9 is not separated from the insertion tube 2 even when the insertion tube 2 is curved due to the curving of the body cavity wall 51, so that the endless belt 9 can be held in contact with the body cavity wall 51 at all times, thus avoiding damages given to the body cavity wall and an unsatisfactory movement of the endless belt 9.

Description will hereunder be given of the second embodiment of the present invention. Same reference numerals are used to designate same or similar constituent parts, so that explanation will not be duplicated or will be simplified.

FIGS. 4 through 7 show the second embodiment of the endoscope according to the present invention.

The endoscope 1 in the second embodiment is of such an arrangement that an image pickup element is provided in the head, and an image pickup signal detected by the image pickup element is led out of the insertion tube to outside through a lead wire for example, whereby the image guide comprising a plurality of optical fibres as shown in FIG. 1 is removed, so that both the insertion tube and the head can be reduced in outer diameter.

Figure 4:
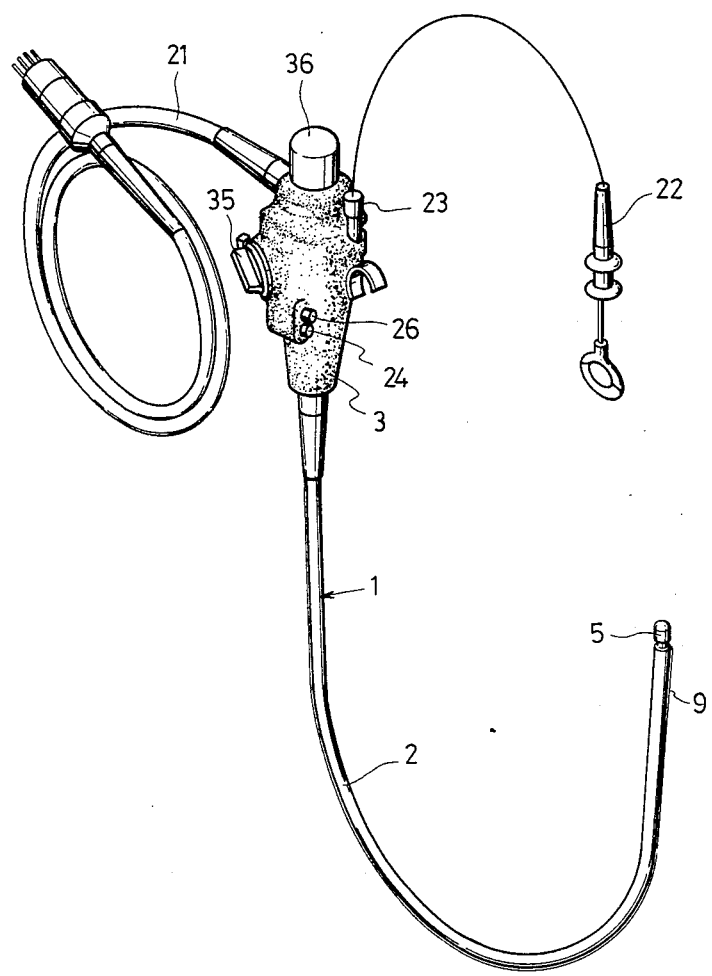
FIG. 4 is a perspective view showing the general arrangement of a second embodiment of the endoscope according to the present invention.
Figure 5:
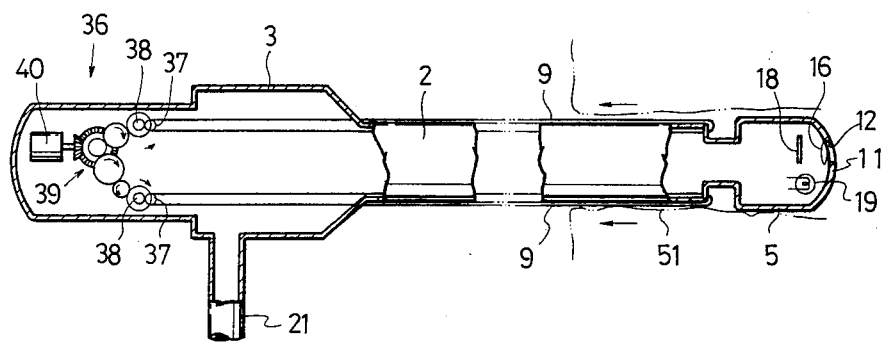
FIG. 5 is a sectional view thereof.
Figure 6:
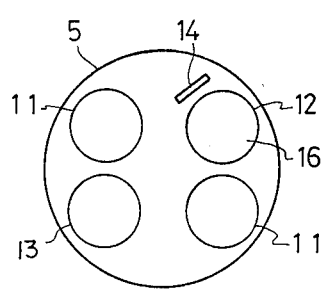
FIG. 6 is a front view showing the forward end face of the head of the insertion tube in the second embodiment.
Figure 7:
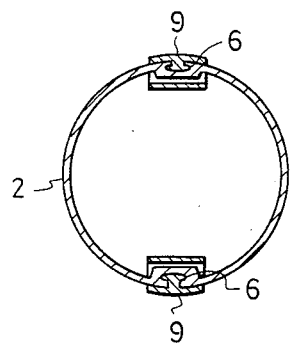
FIG. 7 is a sectional view showing the insertion tube.

Referring to FIGS. 4, 5, and 6 the forward end portion of the insertion tube 2 is flexibly provided thereon with the head 5 through a stepped portion. The head 5 is provided at the forward end face thereof with the picture hole 12, the two projector holes 11, the forceps hole 13 and the air-water feed hole 14, respectively, substantially similarly to the preceding embodiment. In the head 5, there are provided the objective lens 16 and the image pickup element 18, both of which are faced to the picture hole 12, and a light source 19 such as a lamp is faced to the projector hole 11, respectively. In this case, for example, charge-coupled devices are used as the image pickup element 18. On the other hand, as shown in FIG. 7, in the insertion tube 2, there are formed two dovetail groove-shaped guide grooves 6 on the insertion tube 2 at circumferential positions spaced 180° apart from each other on the outer surface and in the longitudinal direction of the insertion tube 2, and there are housed two endless belts 9, a lead wire for transmitting a picture signal detected by the image pickup element 18 to an external device such as a monitoring device, a lead wire for supplying an electric power to the light source 19, a forceps guide tube, the air-water feed tube and the like, respectively. The endless belts 9 are passed through the insertion tube 2, led out of the stepped portion at the forward end of the insertion tube 2 to outside, and guided around the insertion tube 2 to the proximal end thereof along the guide grooves 6 thereon.

In the control portion 3, there is provided a drive means 36 for turning the respective endless belts 9 in directions opposite to each other. The drive means 36 comprises two pairs of guide rollers 37, 38 clampingly holding the opposite surfaces of the proximal ends of the respective endless belts 9 and a motor 40 for turning the guide rollers 38 through a gear train 39 including bevel gears, spur gears and the like, to thereby turn the respective endless belts 9 in directions indicated by arrow marks in FIG. 5.

The method of insertion of the insertion tube according to this embodiment is substantially similar to that according to the first embodiment. However, a difference from the first embodiment resides in that two endless belts disposed in the vertical direction are simultaneously brought into contact with the body cavity wall 51.

The second embodiment described above has the following advantages in addition to the advantages of the first embodiment.

Namely, since two endless belts 9 are provided at positions above and below the insertion tube 2 in the drawing, the contact area of the endless belts 9 contacting the body cavity wall 51 can be increased, so that the period of time required for the insertion of the head 5 can be further decreased. Since a picture signal detected by the image pickup element 18 is transmitted to outside through the lead wire for transmitting the picture signal, necessity for providing the image guide, in which the plurality of optical fibres are bundled, is eliminated, and a space for incorporating the endless belts 9 can be made in the insertion tube 2, whereby the insertion tube 2 can be reduced in diameter accordingly, so that the insertion of the insertion tube 2 and the head 5 into the body cavity can be smoothly effected.

Figure 8:
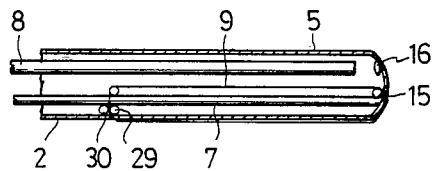
FIG. 8 is a sectional view showing a modification of the scope of guiding the endless belt around.

In working, there is no need for providing the endless belt 9 over the total length of the insertion tube 2, and instead, as shown in FIG. 8 for example, the endless belt 9 may be provided only at the forward end portion of the insertion tube 2 (In order to avoid giving damages to the intestinal wall, it is preferable that the length of the endless belt should be larger than one thirds of the total length of the insertion tube 2). In this case, for example, if the rotation of the motor provided in the control portion 3 at the proximal end of the insertion tube 2 is transmitted to the clamp roller 30 on one side out of the clamp rollers 29 and 30 clampingly holding the opposite surfaces of the endless belt 9 through a flexible rotary shaft, then the endless belt 9 may be turned at the forward end portion.

Figure 9:
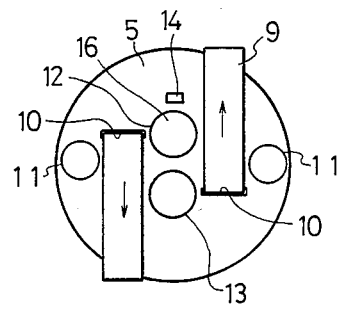
FIGS. 9 to 14 are front views showing modifications of the endless belt, respectively.
Figure 10:
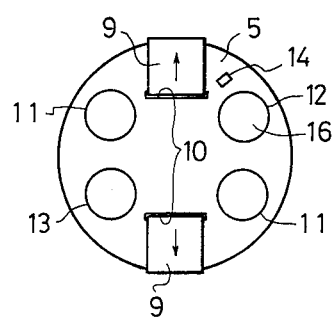

In the first embodiment, there has been described the arrangement, in which one endless belt is used, however, the number of the endless belts need not necessarily be limited to this, but, the arrangement includes the use of two or more endless belts. For example, when two endless belts are used, the endless belts, which have been led out to the outside of the insertion tube 2 from the guide hole 10 and directed to the proximal end of the insertion tube 2, are arranged to turn in directions opposite to each other substantially similarly to the second embodiment as shown in FIGS. 9 and 10.

Figure 11:
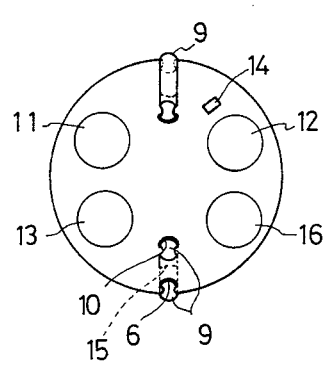
Figure 12:
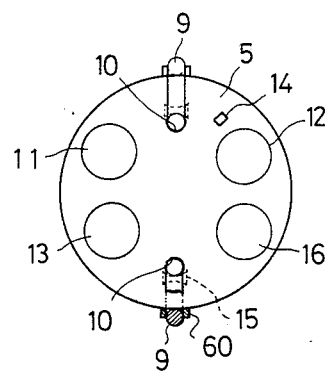

Furthermore, the shape of endless belt need not necessarily be limited to be flat, but, may be round or the like as shown in FIGS. 11 and 12. The endless belt 9 shown in FIG. 11 is formed into a substantially round belt formed with grooves on opposite sides and in the longitudinal direction of the endless belt 9, so that the endless belt 9 is reliably held in the guide grooves 6 to prevent the endless belt 9 from falling off.

Further, in the above embodiment, there has been shown the embodiment, in which the endless belt 9 is slidably coupled into the guide grooves 6, however, projections 60 capable of holding the endless belt 9 from opposite sides thereof may be provided on the head 5 and at a plurality of positions at regular intervals and in the longitudinal direction of the insertion tube 2 as shown in FIG. 12. Furthermore, when the endless belt 9 thus formed of the round belt is used, if the respective pulleys are formed into substantially spool-shapes, then the endless belt may be perfectly prevented from falling off inside and outside of the insertion tube 2, and also, the insertion tube 2 may be prevented from moving in a zigzag fashion, while being inserted.

Figure 13:
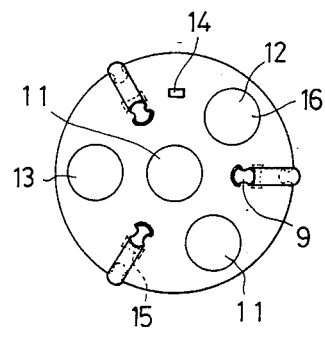
Figure 14:
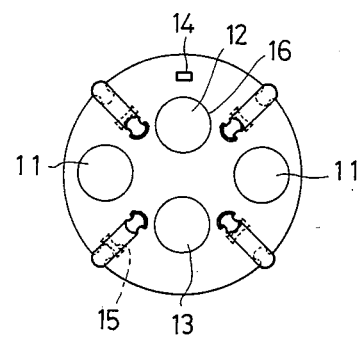

Furthermore, when three or more endless belts 9 are provided, if the endless belts 9 are provided at equiangular positions as centered about the insertion tube 2 as shown in FIGS. 13 and 14, then the insertion tube 2 may be effectively prevented from moving in a zigzag fashion in the vertical and lateral directions.

Figure 15:
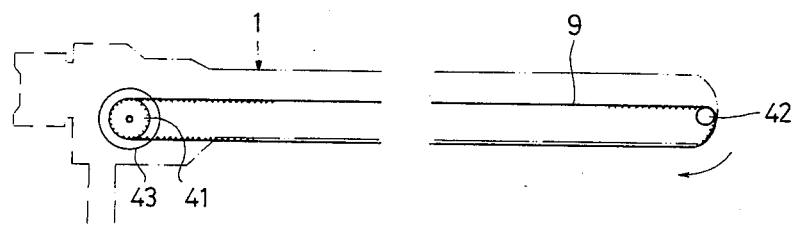
FIGS. 15 and 16 are explanatory views showing modifications of the drive means, respectively.
Figure 16:
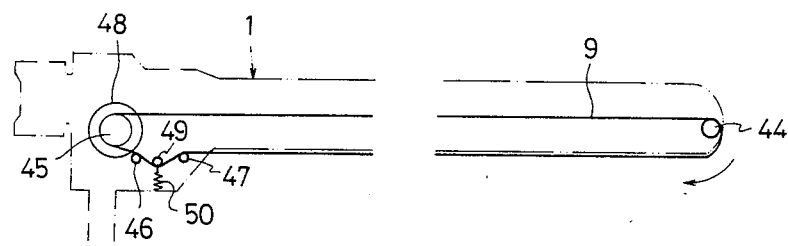

Except the arrangements shown in the abovedescribed embodiments, the drive means 28 and 36 may have arrangements as shown in FIG. 15 or 16. The drive means shown in FIG. 15 is of such an arrangemnet that gears 41 and 42 are provided at the forward end portion and the proximal end portion of the fiber scope 1, respectively, an endless belt 9 formed of a timing belt is guided around these gears 41 and 42, and one 41 of the gears is rotated by a motor 43. Furthermore, the drive means shown in FIG. 16 is of such an arrangement that a plurality of pulleys 44, 45, 46 and 47 are provided at the forward end portion and the proximal end portion of the fiber scope 1, one of the pulleys 45 is rotated by a motor 48 and a tensile force is given to a belt portion between the pullys 46 and 47. A tension mechanism in this case comprises a pulley 49 contacting one surface of the endless belt 9 opposite to the other, which the pair of pulleys 46 and 47 contact, and a spring 50 biasing the pulley 49 toward the pair of pulleys 46 and 47.

In addition, FIGS. 8 through 16 show modifications based on the specific form of the endoscope shown in the first embodiment, by which it is intended to omit the substantially duplicated drawings. Needless to say, the arrangements shown in these drawings are applicable to the second embodiment.

As has been described hereinabove, the present invention can provide the endoscope wherein the insertion tube and the head are reduced in diameter, whereby the endoscope can be smoothly and quickly inserted into a human body without giving considerable pains to a patient.

What is claimed is:

1. An endoscope comprising an insertion tube having a proximal end and a forward end, at least one endless belt extending substantially from the proximal end to the forward end through said insertion tube, said endless belt being partially exposed in the longitudinal direction on the outer surface of said insertion tube and being guided around the proximal end of said insertion tube, and drive means for turning said at least one endless belt provided at the proximal end of said insertion tube.

2. An endoscope as set forth in claim 1, wherein said drive means comprises a pair of rollers for clampingly holding opposite surfaces of said endless belt and a motor for rotating one of said rollers.

3. An endoscope as set forth in claim 1, wherein said endless belt is formed of a flat belt.

4. An endoscope as set forth in claim 1, wherein said endless belt is formed of a substantially round belt.

5. An endoscope as set forth in claim 1, wherein said endless belt comprises a timing belt and said drive means comprises a gear being in meshing engagement with said timing belt and a motor for rotating said gear.

6. An endoscope as set forth in claim 1, wherein said drive means comprises at least two pulleys for stretching said endless belt, a motor for rotating any one of said pulleys and a tension mechanism for giving a tensile force to a belt portion between said pulleys adjacent to each other.

7. An endoscope as set forth in claim 1, wherein said insertion tube is provided with means for preventing said endless belt from falling off and moving in a zigzag fashion.

8. An endoscope as set forth in claim 7, wherein said means for preventing said endless belt from falling off and moving in a zigzag fashion comprises the formation of a groove on said insertion tube portion in the longitudinal direction thereof and the formation of a ridge on said endless belt in a manner to be slidably coupled into said groove.

9. An endoscope as set forth in claim 7, wherein said means for preventing said endless belt from falling off and moving in a zigzag fashion comprises the formation of respective pairs of projections on the insertion tube portion at regular intervals in the longitudinal direction thereof and the holding of said endless belt through said projections.

10. An endoscope wherein an endless belt is guided around a head portion of an insertion tube through pulleys, said endless belt is turned through a drive means and said endless belt is inserted in contact with a body cavity wall, comprising:

a stepped portion is formed at said head portion;

a hole is formed in said stepped portion;

said belt is endlessly guided around between said hole and the proximal end of said insertion tube in a manner to be partially exposed to the outside of said insertion tube; and a drive means for turning said belt is provided in a control portion at the proximal end of said insertion tube.

11. An endoscope as set forth in claim 10, wherein two endless belts are used, which are disposed at positions opposed to each other in the circumferential direction of said insertion tube.

12. An endoscope as set forth in claim 11, wherein said endless belt comprises a round belt, pulleys for supporting said endless belt are each formed into a spool shape, and the outer surface portion of said insertion tube is so formed as to guide said endless belt exposed to the outside of said insertion tube in a predetermined direction.

* * * * *